United States Patent [19]

Maeda et al.

[11] Patent Number: 5,426,042
[45] Date of Patent: * Jun. 20, 1995

[54] KLEBSIELLA OXYTOCA FERM BP-3616 AND IMMOBILIZATION THEREOF WITH A GELATING AGENT IN PORES OF A MEMBRANE

[75] Inventors: Shigeru Maeda; Akira Ohki, both of Kagoshima; Takeshi Sato, Toki; Naho Kato, Chita; Hirofumi Akano, Handa; Yoshiya Kawamura, Kounan; Keizo Hatagaki, Handa; Yasushi Takahashi, Handa; Mikio Yamada, Handa; Hajime Okumura, Handa, all of Japan

[73] Assignee: Nakano Vinegar Co., Ltd., Tokyo, Japan

[ * ] Notice: The portion of the term of this patent subsequent to Oct. 18, 2011 has been disclaimed.

[21] Appl. No.: 179,593

[22] Filed: Jan. 7, 1994

Related U.S. Application Data

[63] Continuation of Ser. No. 978,843, Nov. 19, 1992, Pat. No. 5,356,792.

[30] Foreign Application Priority Data

Nov. 22, 1991 [JP] Japan .................................. 3-307694
Mar. 12, 1992 [JP] Japan .................................. 4-53804
Oct. 14, 1992 [JP] Japan .................................. 4-276363

[51] Int. Cl.⁶ ..................... C12N 11/10; C12N 11/04; C12N 1/12; G01N 27/26
[52] U.S. Cl. ..................... 435/178; 204/403; 435/29; 435/179; 435/182; 435/252.1; 435/817; 435/852
[58] Field of Search ............. 435/29, 177, 178, 180182, 435/252.1, 817, 852, 179; 204/403

[56] References Cited

U.S. PATENT DOCUMENTS

| | | | |
|---|---|---|---|
| 3,684,702 | 8/1972 | Hartmann | 422/79 |
| 4,009,078 | 2/1977 | Wilkins et al. | 435/852 |
| 4,511,657 | 4/1985 | Colaruotolo et al. | 210/64 |
| 4,620,930 | 11/1986 | McDowell et al. | 436/62 |
| 4,761,376 | 8/1988 | Kulpa et al. | 435/262 |
| 4,783,403 | 11/1988 | Araki et al. | 435/852 |
| 5,160,604 | 11/1992 | Nakamura et al. | 210/85 |

FOREIGN PATENT DOCUMENTS

| | | |
|---|---|---|
| 0251320 | 7/1987 | European Pat. Off. . |
| 53-47895 | 4/1978 | Japan . |
| 61-7258 | 3/1986 | Japan . |
| 2129236 | 5/1990 | Japan . |
| 3-123851 | 5/1991 | Japan . |
| 1495378 | 7/1989 | U.S.S.R. . |

OTHER PUBLICATIONS

Akira Ohki, et al., *A Microbial Sensor For Bod Using An Arsenic–Resistant Bacterium*, (Feb. 28, 1992), Analytical Sciences, vol. 7.
Bergey's Manual of Systematic Bacteriology, vol. 1, 1984, pp. 415, 416, 461–465.
Japanese Industrial Standard, *Testing Methods for Industrial Wastewater*, Jan. 03, 1986.

(List continued on next page.)

*Primary Examiner*—David M. Naff
*Attorney, Agent, or Firm*—Pennie & Edmonds

[57] ABSTRACT

A BOD analyzer is prepared having a microbe sensor containing an oxygen electrode and a microbe membrane. The microbe membrane is made by immobilizing microorganisms belonging to the genus *Klebsiella* in the membrane. Specifically, the BOD analyzer has a flow cell equipped with a microbe sensor containing an oxygen electrode and a microbe membrane, and a liquid passage which is connected with an entrance of the flow cell and which is equipped with an outlet. The microbe membrane is made by immobilizing microorganisms belonging to *Klebsiella oxytoca* 12092 strain in a porous hydrophilic membrane having an average pore size of 0.65–3 μm in diameter by using at least one gelating agent selected from alginic acid or salts thereof, agar, gellan gum, xathane gum, gelatine, carageenan, locust bean gum, methylcellulose, pectin, or pullulan. The BOD analyzer can be used for batch or continuous BOD analysis and enables carrying out BOD analysis in a short period of time.

5 Claims, 13 Drawing Sheets

OTHER PUBLICATIONS

Lu-Kwang Ju, et al., *Simultaneous Measurements of Oxygen Diffusion Coefficients and Solubilities in Fermentation Media with Polarographic Oxygen Electrodes*, Biotechnology and Bioengineering, vol. 31, pp. 995–10005 (1988).

*Third European Congress of Biotechnology*, (1984), pp. 151–156.

Abstract of Publication, *Genetic Characteristics of Bacteria Isolated from Stream Water Resistant to Arsenic Compounds*, Chung, McKyung, et al., Coll. Liberal Arts Sci., Kyung Lee Univ., Seoul 130-701 S. Korea Misaengmul Hakhoechi, 29(1), 63-8, 1991.

Abstract of Publication, *Metal Binding Properties of Kiebsiella Oxytoca*, Wallberg M., et al., Dep. Water Environ. Stud., Linkoeping Univ., Linkoeping J–58183, Sweden, Water, Air, Soil Pollution, 57–58, 579–87, (Eng.) 1981.

(A) MICROBE MEMBRANE OF THE INVENTION (3-MINUTE SAMPLE FLOW)
(B) POLYACRYLAMIDE/MICROBE MEMBRANE (30-MINUTE SAMPLE FLOW)

KLEBSIELLA OXYTOCA FERM BP-3616 AND IMMOBILIZATION THEREOF WITH A GELATING AGENT IN PORES OF A MEMBRANE

This is a continuation of application Ser. No. 07/978,843, filed Nov. 19, 1992, now U.S. Pat. No. 5,356,792.

INTRODUCTION

The present invention relates to a biochemical oxygen demand (BOD) analyzer, methods of analysis, and a novel bacterial strain used for analysis. Specifically, the present invention relates to a BOD analyzer comprising a microbe sensor containing an oxygen electrode and a microbe membrane. The microbe membrane is made by immobilizing microorganisms belonging to the genus *Klebsiella* in a membrane.

BACKGROUND OF THE INVENTION

BOD analysis is presently carried out in accordance with Japanese Industrial Standard Method (JIS Industrial Wastewater Test Method K-0102-1972). Since it takes 5 days to analyze BOD, various attempts have been made for quick BOD analysis by utilizing microbe sensors. Among the microorganisms, *Trichosporon cutaneum* and activated sludge have been used as microbes immobilized on the microbe sensors (Japanese Patent Application KOKOKU No. 7258/1986; Suzuki S., ed. Biosensor pp135-136, 140-142 Kodansha Publication (1989)). In addition, an apparatus comprising a flow cell equipped with a microbe sensor has been known as a BOD analyzer (Japanese Patent Application KOKAI Nos. 47895/1978, 123851/1991).

The problem of the microbe sensor is that the BOD result of the microbe sensor has a low correlation to that of the JIS method. The problem is partly because of microorganisms used for microbe sensor. For example, *Trichosporan cutaneum* has a narrow assimilation spectrum on various organic substances, i.e. no response to disaccharides but specific high response to particular substances such as ethylalcohols. In addition, the microbe sensor has been impractical because the sensor has to be activated 1-3 days before BOD analysis in order to have microbes normally respond to samples. When activated sludge is used, activated sludge immobilized on a membrane has to be constantly controlled and the immobilization procedure is required every time the membrane is changed. BOD analysis is unable to carry out using any of the above microorganisms if high concentration of bactericidal substances such as arsenic contained in a sample.

In a BOD analyzer using a flow cell, bubbles remain in samples may affect analysis. In addition, it is necessary to have a more than 30-minute interval from one analysis to another to avoid an affect of a previous sample and it takes a long time to activate microbe membranes stored in a dried condition. Furthermore, maintenance and control of the BOD analyzer are cumbersome; various solutions have to be prepared in a large volume for analysis, which are easily decomposed and are frequently changed.

The present inventors have studied the problems described above and found that microorganisms belonging to the genus *Klebsiella* have the ability to assimilate a variety of organic substances and are activated in a short period of time by an activation procedure, the properties that are suitable for BOD analysis.

Although BOD analysis using a batch processing can be utilized for the present invention, the present inventors found that a micro-flow cell is useful for the BOD analyzer of the present invention because a micro-flow cell is advantageous to short residence time of samples, changes of solutions, and temperature control in a flow cell, the features that make the most of the properties of the microorganism and enable operators to carry out BOD analysis quickly and precisely.

In addition, the present inventors have developed a method of immobilizing microorganisms in a membrane, a BOD analyzer that shorted the time for analysis, a method of activating dried microbe membranes stored for a long period of time, and a method of maintaining the activation level of microorganisms in the microbe membrane using a minimum amount of solutions. These methods have overcome the disadvantages of the method of prior art, resulting in a practical BOD analyzer.

SUMMARY OF THE INVENTION

The present invention is characterized by the following description.

(1). A BOD analyzer comprising a microbe sensor containing an oxygen electrode and a microbe membrane wherein microorganisms belonging to the genus *Klebsiella* are immobilized in a membrane.

(2). The BOD analyzer of (1) in which the microorganisms belonging to the genus *Klebsiella* comprise *Klebsiella oxytoca*.

(3). The BOD analyzer of (1) in which the microorganisms belonging to the genus *Klebsiella* comprise *Klebsiella oxytoca* 12092.

(4). The BOD analyzer of (1) in which the microbe membrane comprises microorganisms belonging to the genus *Klebsiella* and immobilized in a porous hydrophilic membrane having an average pore size of 0.64-3 μm in diameter by using a gelating agent.

(5). The BOD analyzer of (4) in which the microorganisms belonging to the genus *Klebsiella* comprises *Klebsiella oxytoca*.

(6). The BOD analyzer of (4) in which the microorganisms belonging to the genus *Klebsiella* comprises *Klebsiella oxytoca* 12092.

(7). The BOD analyzer of (4) in which the gelating agent comprises at least one agent selected from the group consisting of alginic acids or salts thereof, agar, gellan gum, xathane gum, gelatine, carageenan, locust bean gum, methylcellulose, pectin, and pullulan.

(8). The BOD analyzer of (1) comprising a flow cell equipped with a microbe sensor containing an oxygen electrode and a microbe membrane wherein microorganisms belonging to the genus *Klebsiella* are immobilized in a membrane.

(9). The BOD analyzer of (8) in which a liquid passage connected to the entrance of the flow cell equipped with a microbe sensor is equipped with an outlet.

(10). A BOD analyzer comprising a flow cell equipped with a microbe sensor containing an oxygen electrode and a microbe membrane wherein *Klebsiella oxytoca* 12092 is immobilized in a porous hydrophilic membrane having an average pore size of 0.65-3 μm in diameter by using at least one gelating agent selected from the group consisting of arginic acid or salts thereof, agar, gellan gum, xanthane gum, gelatine, carageenan, locust bean gum, methylcellulose, pectin, and pullulan; and a liquid passage which is connected to the entrance of the flow cell equipped with the microbe sensor and which is equipped with an outlet.

(11). A BOD analysis method of using any one of the BOD analyzer of (1)-(10) wherein, before the use of the BOD analyzer, a nutrition solution is supplied to the microbe membrane, which is then washed for analysis.

(12). A BOD analysis method of using any one of the BOD analyzer of (1)-(10) wherein a washing solution or a substrate solution is intermittently supplied to the microbe membrane when the BOD analyzer is not used for a long period of time.

(13). A BOD analysis method of using any one of the BOD analyzer of (1)-(10) wherein boric acid or sorbic acid or salts thereof are added to a BOD sample.

(14). A BOD analysis method of using the BOD analyzer of (10) wherein, before the use of the BOD analyzer, a nutrition solution is supplied to the microbe membrane, which is then washed for analysis, and wherein a washing solution or a substrate solution is intermittently supplied to the microbe membrane when the BOD analyzer is not used for a long period of time, and wherein boric acid or sorbic acid or salts thereof are added to a BOD sample.

(15). A novel strain *Klebsiella oxytoca* 12092 belonging to *Klebsiella oxytoca* which has a broad assimilation spectrum and is resistant to arsenic.

The present invention provides a BOD analyzer that is useful for quick and precise BOD analysis and easy for maintenance and control.

DEFINITIONS AND ABBREVIATIONS

Figure 1:
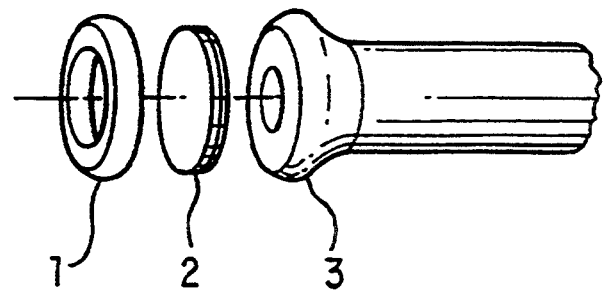
FIG. 1 shows a microbe sensor of the present invention. The microbe sensor comprises an oxygen electrode 3 having contact with a microbe membrane 2 and cap 1 capping the electrode from the top.

1; cap
2; microbe membrane
3; oxygen electrode
4; sample container
5; magnetic valve
6; liquid feeder pump
7; flow cell
8; microbe-sensor
9; stirring rod
10; motor
11; drainage tank
12; washing solution tank
13; amplifier
14; recorder
15, 16, 17. 18, 19; switch valve
AP; air pump
P; liquid-feeder pump

DETAILED DESCRIPTION OF THE INVENTION

Microorganisms used in the present invention are any microorganisms belonging to the genus *Klebsiella*. These microorganisms include *Klebsiella oxytoca* JCM1665, *Klebsiella planticola* JCM7251, *Klebsiella ozaenae* JCM1663, and *Klebsiella terrigena* JCM1687. The present inventors have searched microorganisms in nature suitable for BOD analysis and found a bacterium isolated from soil in Kagoshima prefecture. The bacterium has a broad assimilation spectrum and is able to analyze BOD in a short period of time.

The properties of the bacterium are described below.

A. Morphology (1) Shape and size of the cell: bacilliform, size 0.8–1.2 $\mu m \times 3$–6 $\mu m$;
(2) Polymorphism;
(3) Motility:
(4) Sporulation:
(5) Gram staining:
(6) Acid-fast:

B. Culture Medium (1) Agar plate containing meat extract: grow well, form slightly blue gray colonies.
(2) Slant agar culture containing meat extract: grow well
(3) Liquid medium containing meat extract: grow well
(4) Stab culture containing gelatin: no liquefaction (5) Litmus milk culture medium: acidification and solidification C. Physiology

| | |
|---|---|
| (1) Reduction of nitrate: | + |
| (2) Denitrification: | + |
| (3) Methyl red test: | − |
| (4) Voges-Proskauer test: | + |
| (5) Indole test: | + |
| (6) Hydrogen sulfide production: | − |
| (7) Hydrolysis of starch: | − |
| (8) Citric acid utilization: | − |
| (9) Inorganic nitrogen utilization: | + |
| (10) Pigmentation: | − |
| (11) Urease: | + |
| (12) Oxidase: | − |
| (13) Catalase: | + |
| (14) Growth condition: temperature 5–40° C., pH 4–9.5 | |
| (15) Respiration: facultative anaerobe | |
| (16) Oxidation-fermentation test: fermenter | |

D. Acid or Gas Generation

| Medium | Acid | Gas |
|---|---|---|
| (1) L-arabinose | + | + |
| (2) D-xylose | + | + |
| (3) D-glucose | + | + |
| (4) D-mannose | + | + |
| (5) D-fructose | + | + |
| (6) D-galactose | + | + |
| (7) Maltose | + | + |
| (8) Sucrose | + | + |
| (9) Lactose | + | + |
| (10) Trehalose | + | + |
| (11) D-sorbitol | + | + |
| (12) D-mannitol | + | + |
| (13) Inositol | + | + |
| (14) Glycerine | + | + |
| (15) Starch | − | − |

E. Other Physiological Properties

| | |
|---|---|
| (1) β-galactosidase: | + |
| (2) DNase: | − |
| (3) Tryptophan deaminase: | − |
| (4) Decomposition of esculin: | + |
| (5) Decomposition of arginine: | − |
| (6) Decarboxylation of lysine: | + |
| (7) Decarboxylation of ornithine: | − |
| (8) Arsenic resistance: viable in the presence of 10,000 ppm arsenic | |

The bacterium was classified by Bergey's Manual of Systematic Bacteriology Volume 1, pp 415–416, pp 461–465, 1984, based on the properties described above. The bacterium was identified as a bacterium belonging to *Klebsiella oxytoca* and was designated as *Klebsiella oxytoca* 12092. *Klebsiella oxytoca* 12092 was deposited with Fermentation Research Institute, Agency of Industrial Science and Technology, Ministry of International Trade and Industry of 1-3, Higashi 1-chome, Tsukuba-shi, Ibaraki-ken 305 Japan, under the Budapest Treaty on Oct. 22, 1991, and was assigned the accession number FERM BP-3616.

*Klebsiella oxytoca* 12092 can be cultured by any of the typical culture method for bacteria. Carbon sources of culture include any one of glucose, maltose, sucrose, and molasses or a combination thereof.

Nitrogen sources of culture include any one of organic nitrogen containing substances, such as various amino acids, corn steep liquor, malt extract, peptone, yeast extract, meat extract, and urea, and inorganic nitrogen containing substances, such as ammonium chloride, ammonium sulfate, ammonium nitrate, or a combination thereof.

Vitamins and minerals are also included in a culture medium. Suitable culture temperature may be 20°–40° C., preferably 28°–37° C. Suitable medium pH may be 4.5–9.0, preferably 5.5–8.0. Growth culture may be liquid or solid. Suitable bacterial cells for a microbe sensor material can be obtained at a log phase of growth. Suitable incubation time in a liquid culture may be 10–72, hours, preferably 12–48 hours under aeration conditions. Suitable incubation time in a solid culture may be 12–96 hours, preferably 24–72 hours. After growth, bacterial cells can be harvested by the method known in the art, e.g., centrifugation.

Bacterial cells are washed and then immobilized. For immobilization, the immobilization method known in the art can be used in which bacterial cells are placed between two permeable membranes and then two membranes are stuck to trap the bacterial cells. However, these immobilization methods are liable to detachment in a long period of repeated use. The immobilization method of the invention is preferable in which bacterial cells are immobilized by a gelating agent on a porous hydrophilic membrane having an average pore size of 0.65 μm–3 μm in diameter.

A membrane, a support for immobilization of bacterial cells, used in the present invention includes any gas or liquid permeable, porous hydrophilic membranes. The membrane is required to freely pass oxygen, various organic compounds, and various inorganic compounds. For example, membrane filters and asymmetric ultra-filtration membranes can be used. Membrane materials include cellulose ester compounds such as nitrocellulose and acetylcellulose, and hydrophilic polyfluoride vinylidene and polyether sulfone. Porous hydrophilic membranes used in the invention are needed to be flexible and moldable to fit the form of the surface of an oxygen electrode because membranes are used as a part of a biosensor element and must be fully contact with the surface of the oxygen electrode to have good sensitivity.

Porous membranes used in the invention are preferably an average pore size of 0.65–3 μm in diameter so as to maintain bacterial cells trapped between the pore structure. When asymmetric ultra-filtration membranes are used, the average pore size of 0.65–3 μm in diameter in the top side of the membrane, that is, a larger pore size side of the membrane, is sufficient to be used in the invention. The thickness of membranes is selected by uses, and is preferably 50 μm–200 μm, the thickness that gives good manipulativeness, flexibility, and strength.

A gelating agent used to immobilize bacterial cells in the membrane includes any hydrophilic substances that form gel. For example, alginic acid or salts thereof, gellan gum, xanthane gum, gelatine, carageenan, locust bean gum, methylcellulose, pectin and pullulan are suitable as a gelating agent.

The method to immobilize bacterial cells in a membrane is described below.

Microorganisms grown in a suitable culture medium are harvested, washed, and then immobilized. Microbial cells are combined with an appropriate amount of an gelating agent such as an alginic acid solution to give a microbe/gelating-agent mixture. The mixture is dripped on a porous membrane such as acetylcellulose membrane filters. Suction is applied from the bottom side of the membrane and pressure is applied from the top side of the membrane to have the mixture enter the pore, thereby immobilizing microbes with the gelating agent in the pore. Suction and pressure are kept applying to the membrane so as to ensure that all of the microbe/-gelating-agent mixture on the surface of the membrane is trapped in the pore and are firmly retained in the pore. Strength of suction and pressure is such that porous membranes are not destroyed.

Microbes coated with a gelating agent are trapped in the pore of the membrane and the gelating agent is then solidified using a suitable agent to fix the microbes in the pore. The microbe immobilized in the membrane are not easily detached from the membrane. Agents to solidify gelating agents include inorganic salts such as calcium and polymerization agents. Alternatively, refrigeration can be used to solidify a microbe/gelating-agent mixture.

In the immobilization method described above, a trace amount of a gelating agent is sufficient. For gelation, it takes only a short time at room temperature, the mild condition which can help keep the activation of microorganisms at a high level without damaging the microbes.

The microbe membrane is permeable to oxygen, various inorganic and organic compounds and, if part of the microbe membrane is damaged, only a very small amount of microbes is lost. In addition, the microbe membrane is durable compared to those known in the prior art. The microbe sensor of the BOD analyzer of the present invention comprises a microbe membrane and an oxygen electrode. The microbe membrane is firmly contact with the oxygen electrode by a removable cap, which makes the operator easier to change the microbe membrane. The microbe membrane has a significant sensitivity for detection even in a small amount of a sample. To shorten the time of analysis, a sample volume added to the flow cell may be 1 ml or less, preferably reduced to 0.3–0.6 ml. In addition, the flow cell can be vertically positioned. A sample is supplied from the bottom side of the flow cell with stirring the sample in the flow cell by the stirring rod, and is drained the sample from the top side of the flow cell. By vertically positioning the flow cell, reliable BOD analysis can be carried out because bubbles do not attach to the microbe membrane and bubbles are eliminated from the flow cell. For example, one sample can be analyzed in about 5 minutes at 30° C. when the sample is applied at 4 ml/min. on the apparatus schematically shown in FIG. 2.

In the BOD analyzer of the present invention, it is desirable to set up an outlet at the liquid passage connected to the entrance of the flow cell equipped with the microbe sensor. In the BOD analyzer of the prior art, each inlet of washing solutions, buffers, BOD standard, and a sample is directly connected with the passage to the flow cell, the design that makes quick analysis impossible. For example, when a first sample analyzed is high BOD, the sample remains in the passage. If a second sample to be analyzed is low BOD, the operator has to wait until the first sample does not affect the BOD analysis of the second sample. The present inventors have solved this problem by setting up an outlet at the liquid passage connected to the entrance of the flow cell.

Figure 3:
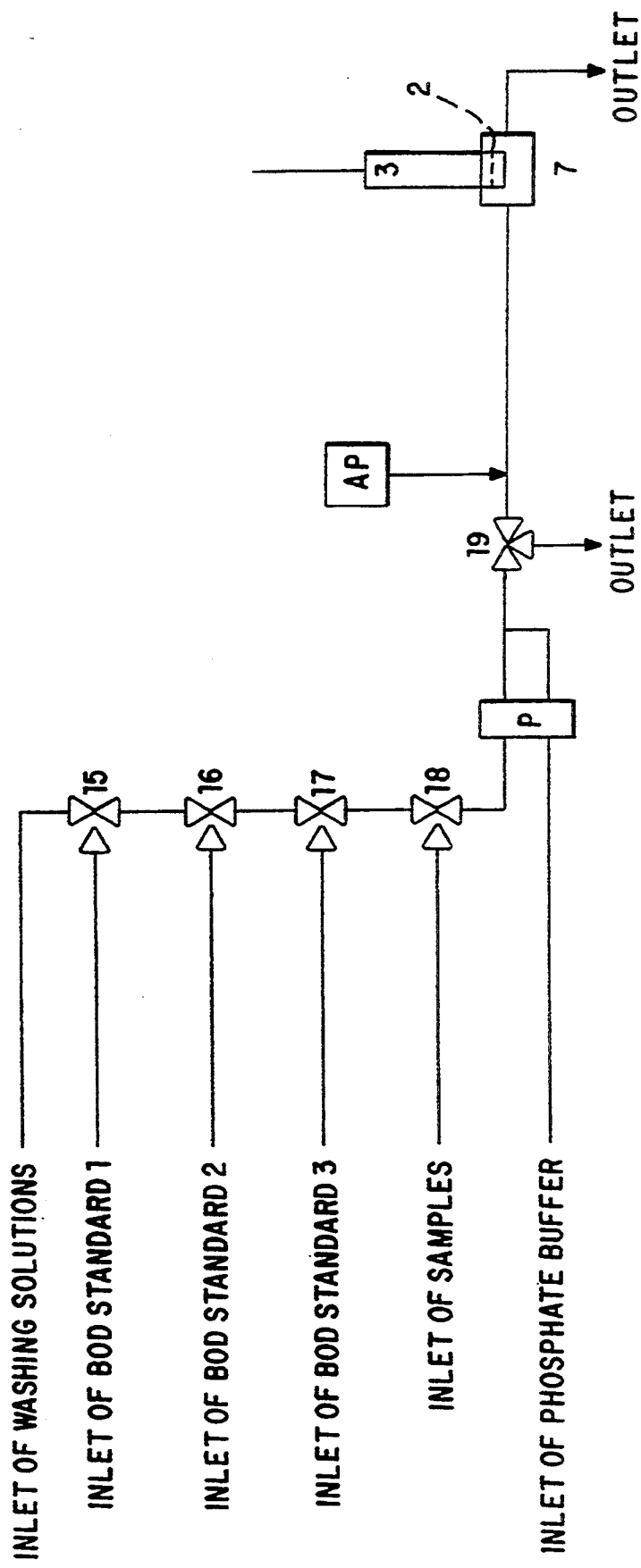
FIG. 3 shows a flow diagram showing the BOD analyzer of the present invention in which a liquid passage connected to the entrance of the flow cell equipped with a microbe sensor is equipped with an outlet.

FIG. 3 shows the design of the BOD analyzer of the invention. In FIG. 3, the numbers (15)–(19) are magnetic switch valves. P is a liquid-feeder pump, which concurrently sends washing solutions, BOD standards, or a sample and phosphate buffer to the flow cell. Washing solutions include tap water, distilled water, and deionized water. Buffers include a phosphate buffer comprising potassium dihydrogen phosphate ($KH_2PO_4$) and dipotassium hydrogen phosphate ($K_2HPO_2$). The concentration of the buffer is typically 50–300 mM, preferably 130–260 mM. The pH of the buffer is adjusted to pH 5.0–8.0, preferably 6.0–7.0, depending on microorganisms to be utilized. Other buffers containing potassium dihydroen phosphate and disodium hydrogen phosphate ($Na_2HPO_4$) can be used.

BOD standard is a mixture prepared using 150 mg/L glucose, 150 mg/L glutamic acid and is adjusted to 220 ppm. 220 ppm BOD standard is diluted to have a desirable concentration.

After passing the liquid-feeder pump, washing solutions, BOD standards, phosphate buffer and a sample are mixed. AP is an air pump supplying air to the mixture passed the valve 19 to allow BOD standards and the sample to contain the same amount of dissolved oxygen, and also serves to remove the effect of oversaturated oxygen. The number (3) is an oxygen electrode and its tip (2) is a microbe membrane. The number (7) is a flow cell having the entry and exit of solutions.

The advantages of the BOD analyzer of the present invention are described below. For instance, time required a sample flowing from the entrance of the sample container to the valve 18 is assumed to be X. Time required a sample flowing from the valve 18 to the valve 19 is assumed to be Y. When analysis of a first sample is completed and a second sample is placed in the sample feeder, the valve 19 opens for X or more minutes and, at the same time, the valve 18 opens. Subsequently, the valve 18 closes for Y minutes and the valve 15 opens for Y or more minutes to flush washing solutions. The mechanism of the BOD analyzer of the present invention prevents the first sample from flowing to the flow cell. Instead, the first sample is drained from the valve 19 and the second sample fills the passage from the sample feeder to the valve 18. The second sample is ready for analysis.

When the valve 19 opens, air is supplied to the flow cell from the air pump (AO), which makes the baseline of output unstable. But, after Y minutes, the valve 19 closes and washing solutions are sent to the flow cell, making the baseline stable.

In the BOD analysis of the present invention, it is preferable to supply nutrition sources to the microbe membrane and then wash the membrane prior to use. These procedures before analysis shorten the activation time of the microbe membrane. The microbe membrane is stored in a dried form to maintain the activation level of the microbes for a long period of time. To activate dried microbe membranes to be used for analysis, the microbe membranes must be changed from a dried form to a wet form. In the method known in the prior art, microbe membranes are soaked in buffer and are then placed in an oxygen electrode, followed by continuous supply of BOD standard until stable output is obtained. It takes two days to be used for analysis in the prior method.

The present inventors have studies methods that shorten the activation time of microbe membranes. In the method of the present invention, microbe membranes are soaked in water or buffer that is used for analysis and then placed in the oxygen electrode. Then, solutions containing nutrition sources (hereinafter referred to as "nutrition solutions") are poured in any one of the inlets of the BOD standards 1,2, 3, or the sample feeder. After a certain period of time, washing solutions and nutrition solutions are alternately flushed.

The flushing time of washing solutions or nutrition solutions is 30 seconds to 30 minutes, preferably about 10 minutes. The composition of the nutrition solution is one typically used for culturing microorganisms or one suitable for growth of microorganisms in membranes. Carbon sources include monosaccharides such as glucose and fructose, and disaccharides such as sucrose and maltose. Nitrogen sources include ammonium salts such as ammonium chloride and ammonium sulfate, various amino acids and polypeptones. Vitamins include yeast extract and trace elements include metal salts such as magnesium sulfate and iron sulfate.

Alternatively, nutrition solutions are a BOD standard solution containing yeast extract as a vitamin source, and metal salts can be added to the solution, if necessary. These nutrition solutions comprising a BOD standard solution and yeast extract contain glucose, glutamic acid and yeast extract. In the nutrition solution, the concentration of glucose or glutamic acid is 5-1,000 ppm, preferably 300-600 ppm, and the concentration of yeast extract is 10-10,000 ppm, preferably 200-400 ppm. Phosphate necessary for the growth of microorganisms is supplied by a phosphate buffer.

In the BOD analysis method of the present invention, it is preferable to intermittently supply washing solutions or substrate solutions to the microbe membrane when the microbe membrane is not used for a long period of time. By supplying the solutions, the microbe membrane is kept active for a long period of time in a small amount of solutions. Generally, nutritions are believed to be supplied from organic materials in a sample when microbe membranes are used for analysis. Nutritions are not supplied to microbe membranes, thereby reducing the activation level of microbes when microbe membranes are not used for analysis. To maintain the activation level of microbe membranes, nutrition sources are kept supplying to microbe membranes when microbe membranes are not used for analysis. One of the method of supplying nutritions to microbe membranes is one where washing solutions and BOD standard solutions are continuously supplied to microbe membranes, as is done when BOD standard is analyzed. In this method, there are two alternatives: the nutritional supply is all of the BOD standard used for analysis, or the nutritional supply is a single concentration of BOD standard. But this method requires a plenty of BOD standard solutions, washing solutions, and buffers, even if one of the alternatives is taken. For example, approximately 5 liters of a combined volume (washing solutions, BOD standards, buffers) are consumed for 16-hour operation at a flow rate of 5 ml/min. Thus, frequent preparation of the solutions as well as time for the preparation are required so that BOD analysis becomes cumbersome in this method.

The present inventors have found that intermittent supply of nutrients in a minimum amount that keeps the activation level of microbe membranes is sufficient for maintaining the activation level of microbe membranes, rather than supplying nutrients continuously. In the intermittent nutrient supply method, a pump is operated for a certain period of time and then stopped for a certain period of time. Washing and substrate solutions are alternately supplied in a certain cycle during operation. Pumping time is 10 seconds to 4 minutes, preferably 30 seconds to 2 minutes, depending on the properties of microorganisms. Pumping stops for 30 seconds to 3 minutes, preferably 1-2 minutes. Substrate solutions supplied to microbe membranes may include BOD standards and nutrition solutions containing the nutrients described above. The method of supplying washing and substrate solutions is such that alternate supply of washing solutions and substrate solutions, or 10 series of supply of washing solutions followed by one supply of substrate solutions, or various combinations of supply of these solutions. This method does not require frequent preparation of various solutions, which makes the control of the BOD analyzer of the invention easier.

In the BOD analysis method of the invention, it is preferable to add boric acid, sorbic acid or salts thereof to solutions used for BOD analysis. Generally, hydrochloric acid or acetic acid is added to a solution used for BOD analysis to reduce pH to prevent the solution from putrefaction.

Alternatively, sodium hypochlorite or other chemicals are added to reduce the pH of the solution and chloramphenicol is then added. Preservatives should be those that have the least effect on microorganisms in the membrane.

The present inventor have found that, among various preservatives, boric acid ($H_3BO_3$) or sorbic acid or salts thereof are suitable for microbe membranes. Salts of boric acid or sorbic acid include sodium borate, potassium sorbic acid. Boric acid and potassium sorbic acid are preferable. The concentration of the preservative varies: The concentration of boric acid is 0.1-1.0%, preferably 0.3-0.5%, and the concentration of sorbic acid is 0.1-1.0%, preferably 0.25-0.5%. In addition, boric acid and low pH is a good combination for the prevention of putrefaction. The pH is adjusted to 2-3 with inorganic acids such as hydrochloric acid and the like or organic acids that are not metabolized by microorganisms in the microbe membrane to improve putrefaction prevention.

This method does not require frequent preparation of various solutions, which makes the control of the BOD analyzer of the invention easier.

EXAMPLE

The present invention will be understood more readily with reference to the following examples; however these examples are intended to illustrate the invention but are not constructed to limit the scope of the invention.

EXAMPLE 1

Culture of *Klebsiella oxytoca* 12092 (FERM BP-3616)

*Klebsiella oxytoca* 12092 (FERM BP-3616) was aseptically inoculated into 100 ml of a sterilized liquid medium/pH 6.5 (1% polypeptone, 0.1% yeast extract, 0.5% sodium chloride) in a 500-ml erlenmeyer flask and was incubated with shaking under aerobic conditions at 30° C. for 24 hours. After growth, bacterial cells were harvested by centrifugation at 6,000 rpm for 20 minutes. The bacterial cells were suspended in a small amount of sterilized water and the suspension was centrifuged at 6,000 rpm for 20 minutes (washing). The washing procedure was repeated three times and 150 mg bacterial cells (dry weight) were obtained.

EXAMPLE 2

Oxygen Consumption Rate of *Klebsiella oxytoca* 12092 (FERM BP-3616) and Various Other Bacteria An oxygen consumption rate of *Klebsiella oxytoca* 12092 (FERM BP-3616) obtained in Example 1 and of various other bacteria cultured by the same manner as described in Example 1 was analyzed using a BOD standard solution. 250 ppm BOD standard solution was prepared using 150 mg/l glucose and 150 mg/l glutamic acid as is described in JIS K0102 and was diluted when necessary. This diluted BOD solution is hereinafter referred to as "BOD standard".

TABLE 1

| Strain of bacterium | Oxygen consumption rate* (mg $O_2$/min./g in dry weight) |
| --- | --- |
| *Klebsiella oxytoca* 12092 | 4.3 |
| *Klebsiella oxytoca* JCM1665 | 4.0 |
| *Klebsiella ozaenae* JCM1663 | 3.8 |
| *Klebsiella planticola* JCM7251 | 3.2 |
| *Klebsiella terrigena* JCM1687 | 3.5 |
| *Trichosporon cutaneum* IFO 10466 | 2.1 |

*Oxygen consumption rate was analyzed at 30° C. using 37 ppm BOD standard as a substrate.

As is shown in Table 1, microorganisms belonging to *Klebsiella* have a high oxygen consumption rate on BOD standard. Among the microorganisms, *Klebsiella oxytoca* 12092 (FERM BP-3616) has the highest oxygen consumption rate.

EXAMPLE 3

Figure 4:
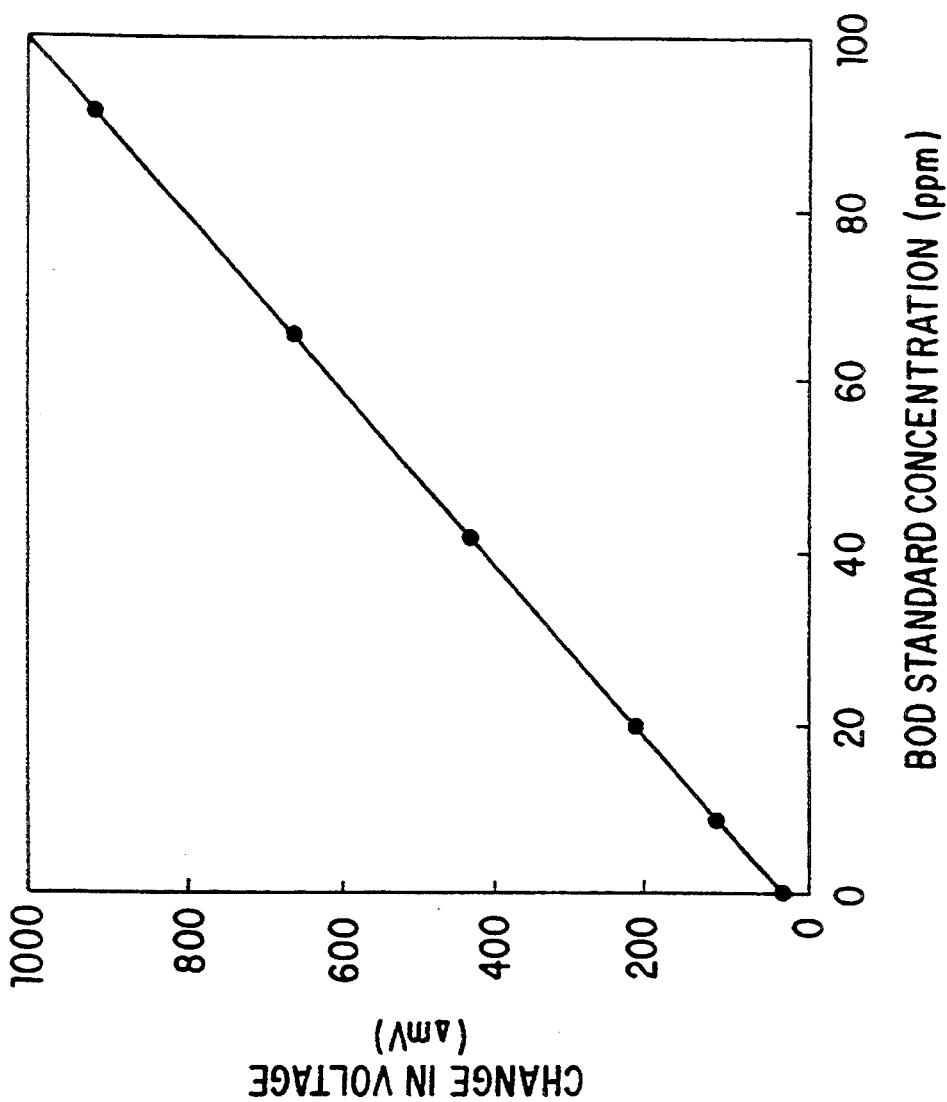
FIG. 4 is analysis of various concentrations of BOD standards using a BOD analyzer in FIG. 2.

Apparatus, Analysis, and Standard Curve 0.4 mg (dry weight) bacterial cells of *Klebsiella oxytoca* 12092 strain (FERM BP-3616) obtained in Example 1 was placed between two nitrocellulose membranes [membrane filter HAWPO2500 (pore size: 0.45 μm in diameter), Millipore Co.,]. The two membranes were firmly stuck together so as not to give any other spaces but bacterial cells (hereinafter the membrane containing bacteria is referred to as "microbe membrane"). The microbe membrane was immersed in 100 mM phosphate buffer/pH7.0 and aerated at 100 ml/minute for three hours using an air pump to activate the microbe membrane. Various concentrations of BOD standards were tested on the apparatus equipped with the microbe membrane shown in FIG. 2. As is shown in FIG. 4, there is a linear correlation between a change in a BOD standard concentration and the corresponding change in voltage measured by the oxygen electrode.

BOD standard was tested by varying its volume in the reaction vessel. The results are shown in Table 2, in which a BOD standard concentration analyzed by the apparatus is one calculated from a change in voltage based on the standard curve shown in FIG. 4. It was found that less than 1 ml of BOD standard gives an appropriate measurement. It takes more time for measurement and washing when more than 1 ml of BOD standard is used. In contrast, measurement is unreliable when less than 0.3 ml of BOD standard is used.

TABLE 2

| | BOD standard concentration (ppm) | Volume in reaction vessel (ml) | | | | | | | |
| --- | --- | --- | --- | --- | --- | --- | --- | --- | --- |
| | | 0.1 | 0.2 | 0.3 | 0.5 | 0.6 | 1.0 | 2.0 | 5.0 |
| BOD found (ppm) | 22 | 10 | 18 | 21 | 21 | 22 | 23 | 21 | 22 |
| | 44 | 20 | 35 | 44 | 44 | 43 | 45 | 44 | 46 |
| | 66 | 50 | 58 | 65 | 66 | 67 | 66 | 67 | 66 |
| | 122 | 98 | 105 | 124 | 123 | 123 | 122 | 125 | 123 |
| Time for analysis* (min.) | | 2 | 3 | 4 | 4 | 5 | 5 | 15 | 20 |

*Time for analysis includes time for washing.

EXAMPLE 4

Comparison of Activation Time

Various bacterial cells obtained in Example 1 were immobilized in a nitrocellulose membrane as described in Example 3 to give a microbe membrane. Immediately after immobilization, the microbe membrane was immersed in a 100 mM phosphate buffer/pH7.0 and aerated at 100 ml/minutes using an air pump to activate the microbe membrane. The activated microbe membrane was taken out periodically and inserted in the device schematically shown in FIG. 2 to test various concentrations of BOD standards. As is shown in Table 3, it takes 1–2 days for *Trichosporon cutaneum* IFO10466 to be activated while it takes only three hour for microorganisms belonging to the genus *Klebsiella*, *Klebsiella oxytoca* 12092 to be activated.

TABLE 3

| | Aeration (hr) | | | | | | | |
| --- | --- | --- | --- | --- | --- | --- | --- | --- |
| | 0 | 1 | 3 | 5 | 10 | 24 | 36 | 48 |
| *Klebstella oxytoca* 12092 (ppm) | 30 | 38 | 65 | 67 | 66 | 67 | 65 | 66 |
| *Trichosporon cutaneum* IFO10466 (ppm) | 4 | 8 | 12 | 11 | 46 | 58 | 60 | 64 |

Values found are those analyzed using 66 ppm BOD standard.

EXAMPLE 5

BOD Analysis of Various Compounds (Comparison of *Klebsiella oxytoca* 12092 Membrane and *Trichosporon cutaneum* Membrane)

The microbe membranes of *Klebsiella oxytoca* 12092 in Example 4 and of *Trichosporon cutaneum* were fully activated and tested to analyze BOD of various compounds. The results were compared to those analyzed by the 5-day BOD method, a method described in JIS K0102. The microbe membranes were tested on the apparatus described in Example 3 and the calibration curve was drawn using BOD standard.

As is shown in Table 4, BOD obtained from the *Klebsiella oxytoca* 12092 membrane is similar to that obtained from the 5-day BOD method, an officially accepted method. The coefficient of correlation ($r^2$) is 0.993. *Trichosporon cutaneum* IFO 10466 does not respond to disaccharides while *Klebsiella oxytoca* 12092 responds to them. When ethyl alcohol is measured, *Trichosporon cutaneum* IFO 10466 has higher BOD than the 5-day BOD method while *Klebsiella oxytoca* 12092 has almost the same BOD as the 5-day BOD method.

TABLE 4

| Test sample | BOD (g/g) | | |
| --- | --- | --- | --- |
| | Microbe sensor of the invention | 5-day method method | Microbe-sensor of *Trichosporon cutanium* IFO10466 |
| Glucose | 0.77 | 0.78 | 0.72 |
| Fructose | 0.74 | 0.71 | 0.54 |
| Sucrose | 0.45 | 0.45 | 0.36 |
| Lactose | 0.45 | 0.45 | 0.06 |
| Maltose | 0.53 | 0.50 | 0.03 |
| Glutamic acid | 0.56 | 0.56 | 0.70 |
| Glycine | 0.15 | 0.10 | 0.45 |
| Ethanol | 0.95 | 0.93 | 2.90 |
| Acetic acid | 0.85 | 0.88 | 1.77 |

EXAMPLE 6

Analysis of BOD Standards in the Presence of Arsenic

Figure 5:
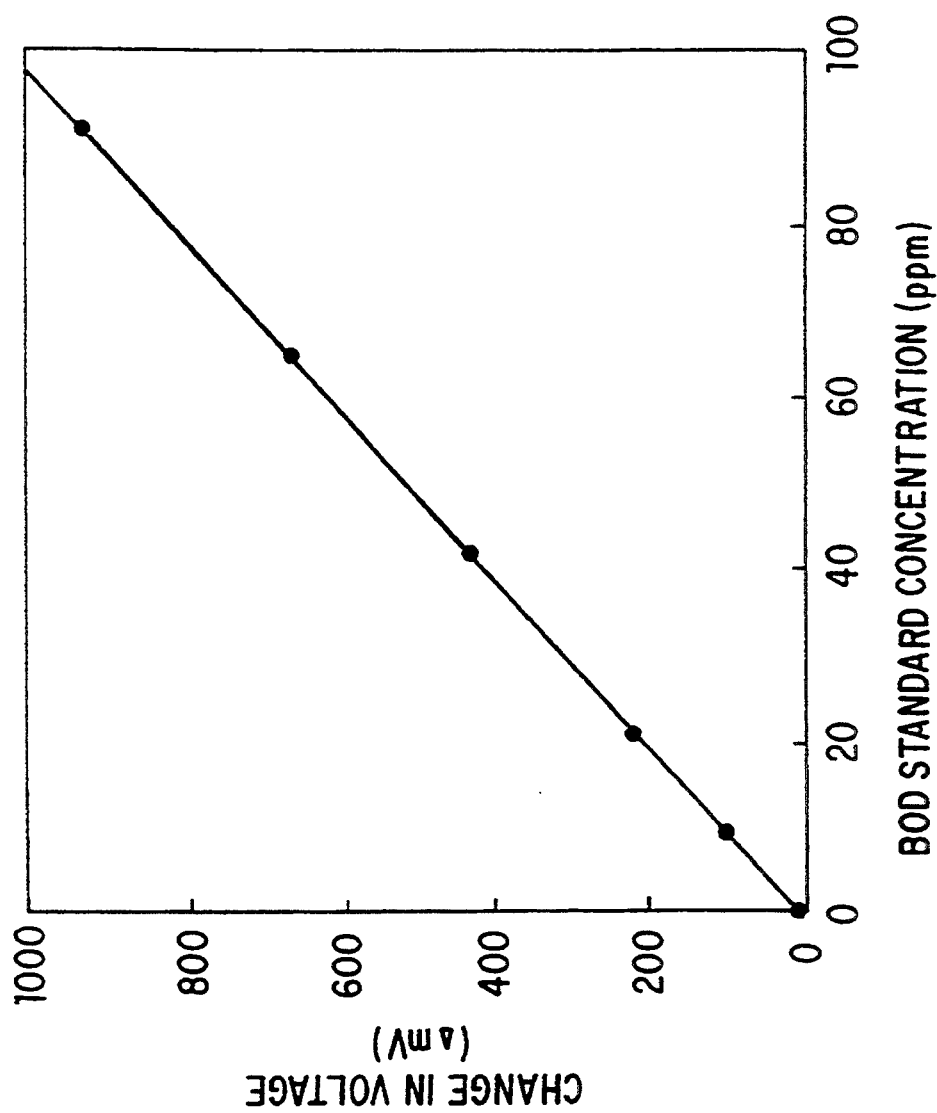
FIG. 5 is analysis of various concentrations of BOD standards in the presence of arsenic using a BOD analyzer in FIG. 2.

Various concentrations of BOD standards were analyzed in the presence of arsenic by a similar method described in Example 3. As is shown in FIG. 5, there is a good linear correlation between a BOD standard concentration and the corresponding change in voltage on the oxygen electrode. As is evident from the results described above, various BOD standards can be precisely analyzed by the present invention in a short period of time.

EXAMPLE 7

Analysis of Wastewater (Comparison of the Microbe Sensor Method of the Invention and the 5-day BOD Method)

Figure 2:
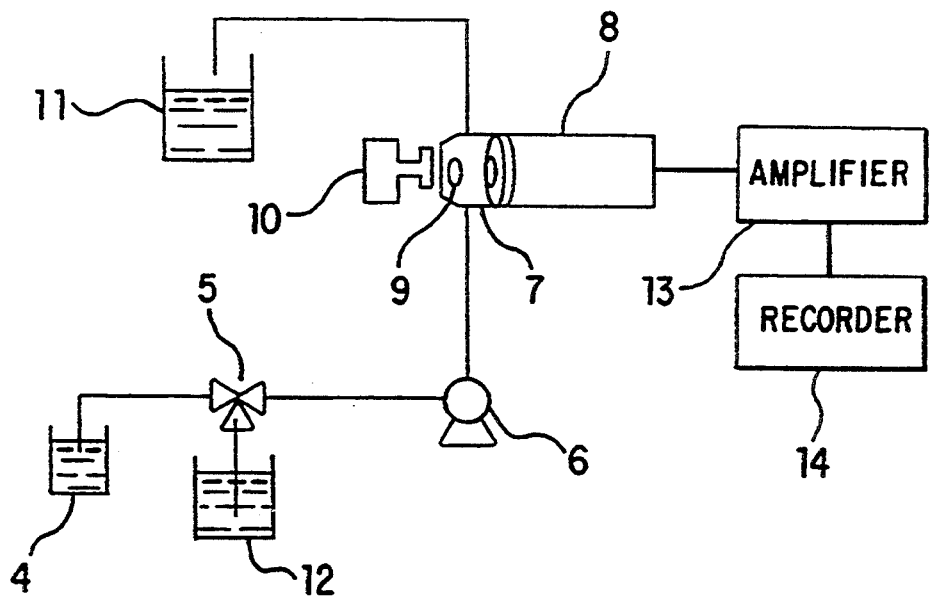
FIG. 2 shows a diagram of the BOD analyzer of the present invention. A BOD sample is sent from a sample container 4 via a magnetic valve 5 and a liquid-feeder pump 6 to a flow cell 7. In the flow cell 7, the sample is stirred by a stirring rod 9 actuated by a motor 10. Changes are detected by a microbe sensor 8 comprising an oxygen electrodes 3 with a microbe membrane 2, both of which are firmly pressed by a cap 1, and are then amplified by an amplifier 13, and are recorded by a recorder 14. The sample flows to a drainage tank 11 after analysis. The magnetic valve 5 is a switch to open a washing solution tank 12 to wash the BOD analyzer.

The activated microbe membrane of *Klebsiella oxytoca* 12092 obtained in Example 3 was inserted in the device shown in FIG. 2. Various wastewaters were tested for BOD using the *Klebsiella oxytoca* membrane and the 5-day BOD method. The comparison of the microbe sensor method and the 5-day BOD method is shown in Table 5. A high correlation is found between the results obtained by the methods.

TABLE 5

| Wastewater sample | BOD (ppm) | |
| --- | --- | --- |
| | 5-day method | Microbe sensor method |
| Swine housing | 1940 | 1880 |
| Sewage disposal plant | 24.2 | 20.0 |
| Sewage purifier | 25.7 | 28.2 |
| Car repair shop | 52.6 | 49.0 |
| Poultry laboratory | 30.3 | 33.8 |
| Food plant | 49.3 | 39.4 |
| Marine product Processing plant | 45.6 | 45.2 |
| Balneotherapy clinic | 60.9 | 60.0 |

EXAMPLE 8

Immobilization of *Klebsiella oxytoca* 12092 in Membranes 0.4 mg (dry weight) bacterial cells of *Klebsiella oxytoca* 12092 strain obtained in Example 1 and 50 μl of a sterilized 3% sodium arginic acid solution were combined.

To immobilize the bacterial cells, the mixture was dipped on an acetylcellulose membrane (membrane filter type HA, average pore size; 0.8 μm in diameter, Millipore Co.,). Suction was applied from the bottom side of the membrane until all the mixture was absorbed by the membrane. The membrane was then immersed in 50 ml of a 5% calcium chloride solution at room temperature for 10 minutes to solidify the arginic acid to immobilize the bacterial cells in the membrane.

EXAMPLE 9

BOD Analysis Using the Apparatus of the Present Invention

Figure 6:
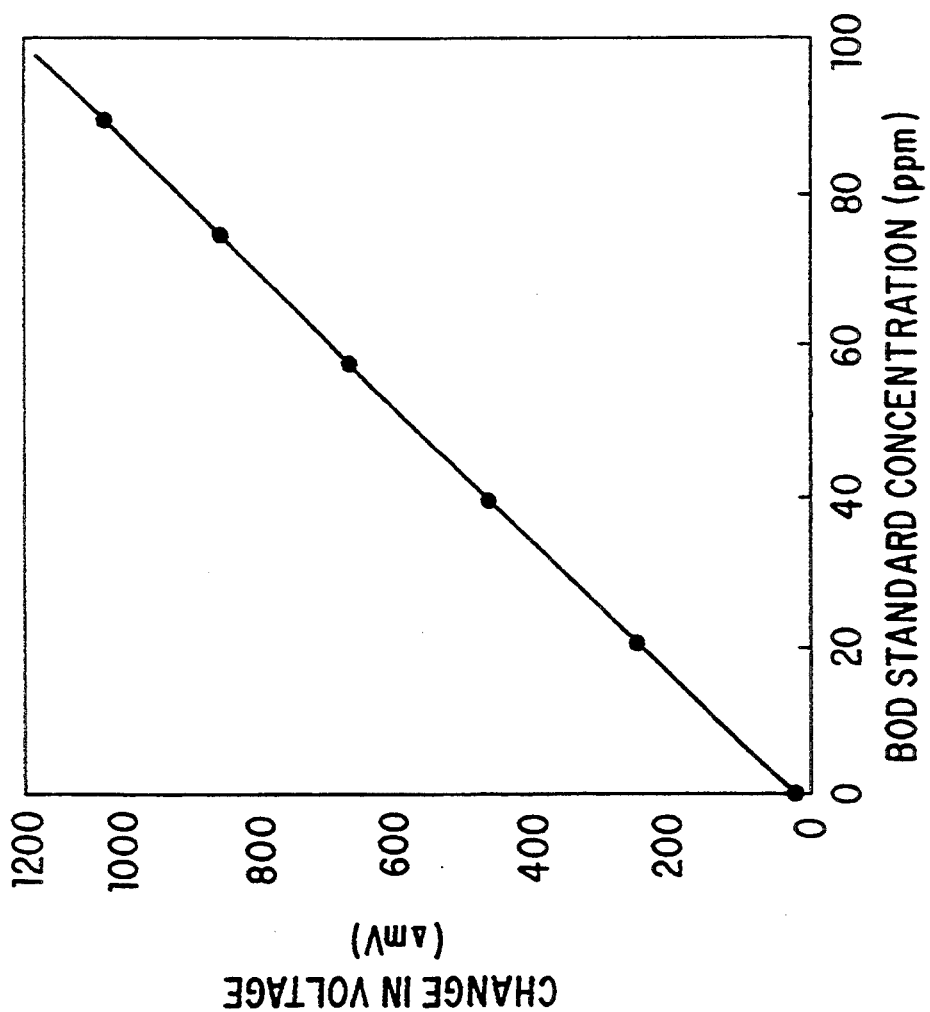
FIG. 6 is analysis of various concentrations of BOD standards using a BOD analyzer schematically shown in FIG 2 wherein microbes are immobilized by a gelating agent.

BOD standard (JIS-KO102) was analyzed using the microbe membrane obtained in Example 8. As is shown in FIG. 1, the microbe sensor is a device comprising the microbe membrane 2 inserted between the oxygen electrode 3 and the cap 1. Analysis was carried out using the apparatus shown in FIG. 2. 10 ml of the sample was analyzed at 30° C. at a flow rate of 3 minutes (3 minutes for analysis). Samples and washing solutions can be aerated, if necessary, or can be aerated on the way to the flow cell 7. As a result of the analysis using the apparatus of the present invention, a good linear relationship between a BOD standard concentration and the corresponding change in voltage of the oxygen electrode was obtained (see FIG. 6). Wastewater collected from a food plant in Kagoshima prefecture was tested for BOD under the same condition as described above by the apparatus of the present invention and the 5-day method. The resulting BOD did not differ one another: BOD was 42 ppm in the apparatus of the present invention and 45 ppm in the 5-day method. The comparison indicate that the apparatus of the present invention can work in the field.

EXAMPLE 10

Comparison of a Pore Size of a Membrane

Figure 7:
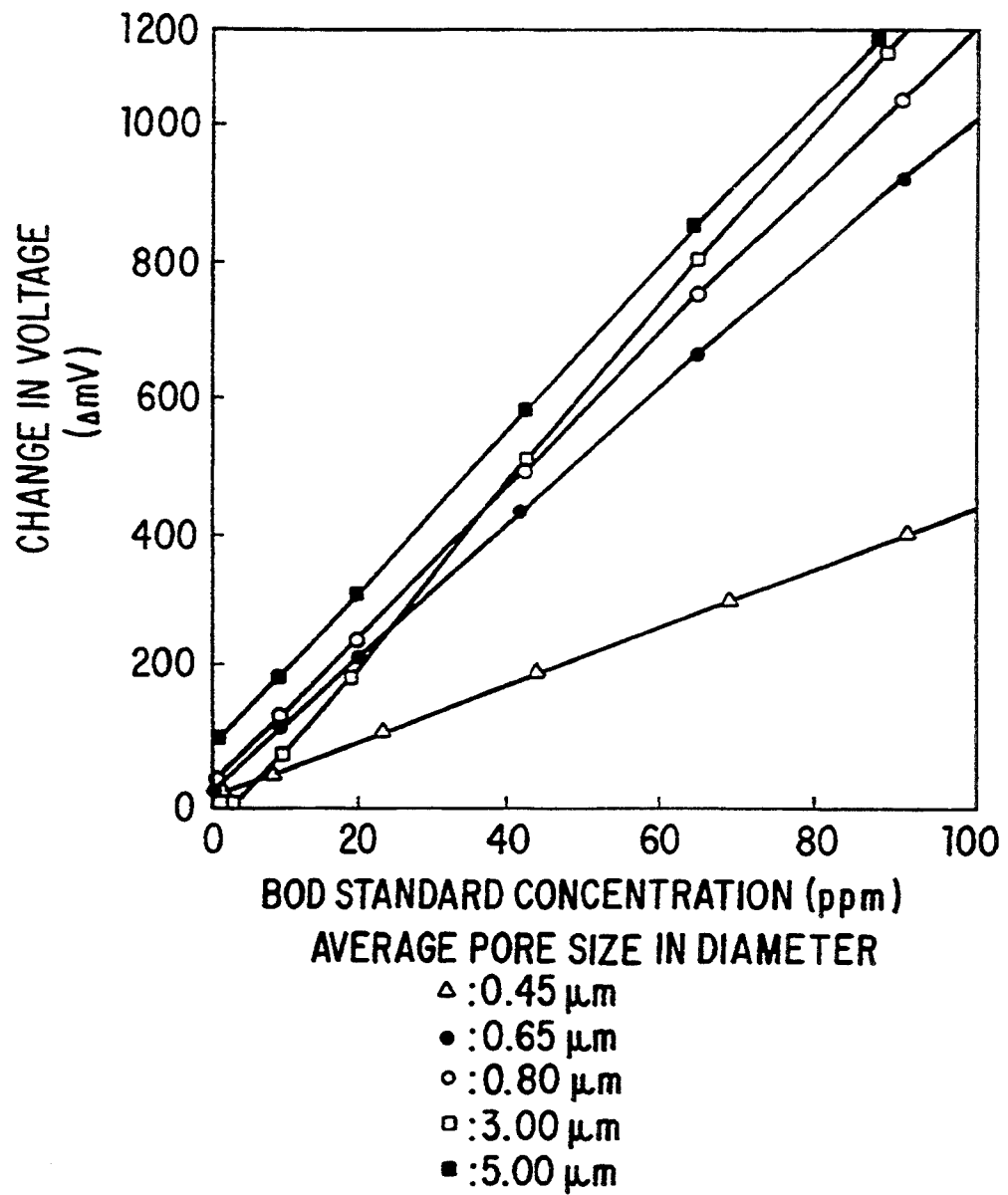
FIG. 7 is analysis of various concentrations of BOD standards using a BOD analyzer schematically shown in FIG. 2 wherein microbe membranes are porous membranes having various average pore sizes in diameter.
Figure 8:
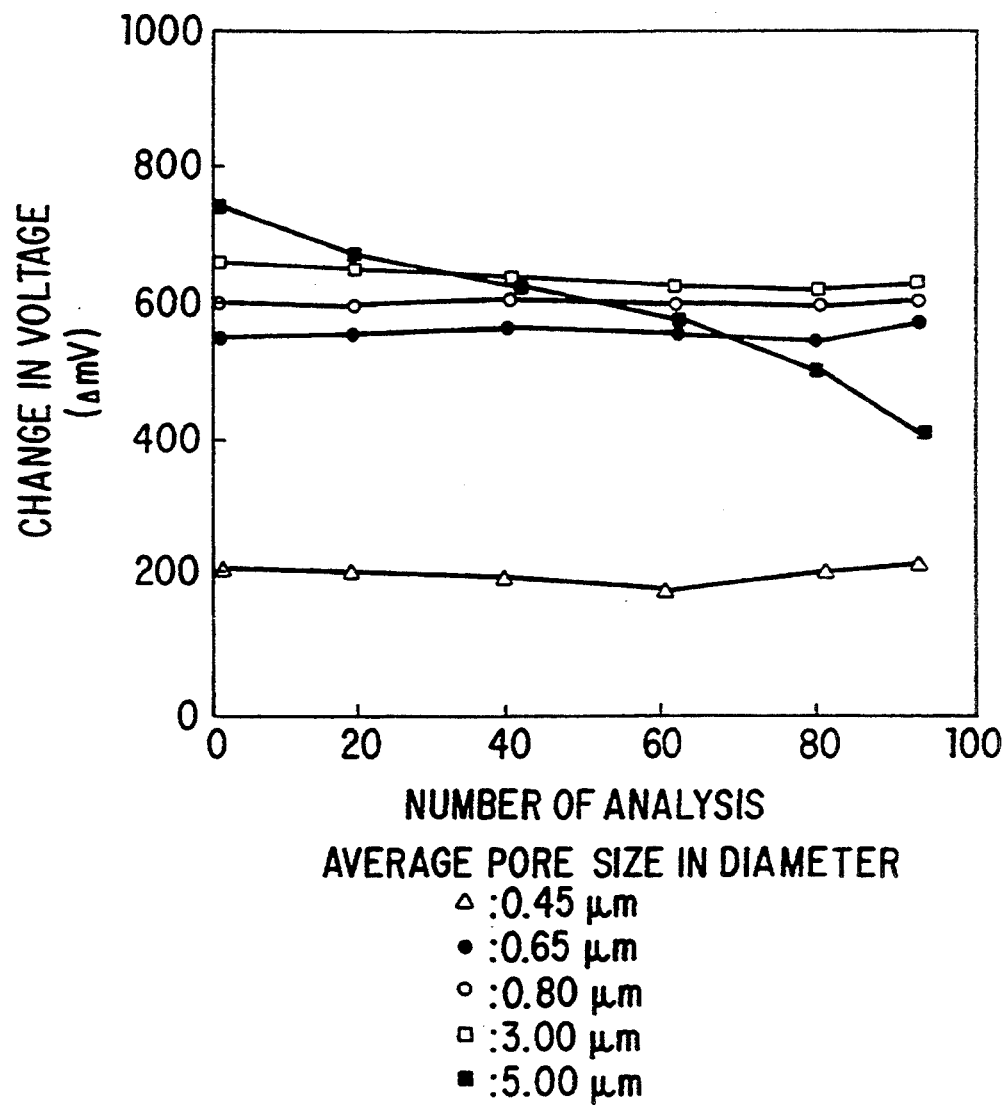
FIG. 8 is analysis of various concentrations of BOD standards using a BOD analyzer schematically shown in FIG. 2 wherein microbe membranes are porous membranes having various average pore sizes in diameter.

Commercially available porous membranes (average pore size is different from the one described above) were used to immobilize bacterial cells obtained in Example 1 by a similar method described in Example 8. The membrane was inserted in the microbe sensor device described in Example 9 and BOD standard was analyzed under the same condition described in Example 9. The analysis of various concentrations of BOD standards are shown in FIG. 7. The repeated analyses of 66 ppm BOD standard are shown in FIG. 8. Microbe membranes made from porous membranes in an average pore size of 0.45 μm in diameter are less responsive. Microbe membranes made from porous membranes in an average pore size of 5 μm in diameter become less responsive when repeatedly used and which are unable to use for another analysis. Microbe membranes made from porous membranes in an average pore size of 0.65 μm or more in diameter provide a good linear relationship between a BOD standard concentration and the corresponding change in voltage of the oxygen electrode. Microbe membranes made from porous membranes in an average pore size of 3 μm or less in diameter provide a stable response when repeatedly used. Taken altogether, microbe membranes made from porous membranes in an average pore size of 0.65–3 μm in diameter provide stable and responsive microbe sensors.

EXAMPLE 11

Comparison of Porous Membranes

Various porous membranes having different average pore sizes in diameter but having 150 μm in thickness were used to make microbe membranes. Bacterial cells free of a gelating agent were dripped onto the porous membranes. Suction was applied from the bottom side of the membrane to trap the bacterial cells in the membrane.

The microbe membrane of the present invention was also made as described in Example 8. Analysis was carried out under the same condition described in Example 10 using the both membranes. As is shown in Table 6, the microbe membrane free of a gelating agent do not have any response compared to the gelated microbe membrane of the present invention. The microbe membrane free of a gelating agent was believed to trap an insufficient volume of bacterial cells so that porous membranes were changed thickness from 150 μm to 600 μm. In addition, a volume of bacterial cells to be trapped was increased to 4 mg (dry weight), 10 times the volume used for the microbe membrane of the present invention. The increased volume of bacterial cells was immobilized by the same method described above.

TABLE 6

| Average pore size in diameter (μm) | 0.45 | 0.65 | 0.8 | 3.0 | 5.0 | 0.8* |
|---|---|---|---|---|---|---|
| Response to 66 ppm BOD standard (ΔmV) | 20 | 60 | 40 | 0 | 0 | 600 |

*Present invention

Table 7 shows the results. Microbe membranes made from porous membranes in an average pore size of 0.8 μm or less in diameter are unable to use for analysis. This is due to the following reason: When analyzing BOD, washing water is flushed to the reaction vessel. Then, a baseline voltage on the microbe electrode, which indicates an initial oxygen concentration, is measured. The baseline voltage measured on the oxygen electrode was 20 mV (see Table 6), indicating almost no oxygen. With almost no oxygen, it is impossible to measure changes of dissolved oxygen concentration that occur when microorganisms assimilate various organic materials.

TABLE 7

| Flow rate of sample | Average pore size in diameter (μm) | | | | | |
|---|---|---|---|---|---|---|
| | 0.45 | 0.65 | 0.8 | 3.0 | 5.0 | 0.8† |
| 3 min. (ΔmV) | — | — | — | 0 | 0 | 600 |
| 30 min. (ΔmV) | — | — | — | 80 | 150 | NA* |
| Baseline voltage (mV) | 20 | 30 | 40 | 200 | 300 | 1000 |

† Present invention
*Not analyzed

No change in oxygen concentration indicates that oxygen in washing water and/or samples can not pass the microbe membrane freely. The baseline voltage of the microbe membrane having an average pore size of 3 μm or more in diameter was 200–300 mV, a fairly high voltage (see Table 7). There was no response to 3-minute flow samples, and little response to 30-minute flow samples. In contrast, the microbe membrane of the present invention was as much as 1000 mV in a baseline voltage and responded to 3-minute flow samples.

The microbe sensor the present invention gives a baseline voltage as much as 1,000 mV and quick response to 3 minute-flow samples. The microbe sensor of the present invention therefore enables quick BOD analysis.

EXAMPLE 12

Comparison of Immobilization Methods of Bacterial Cells

Figure 9:
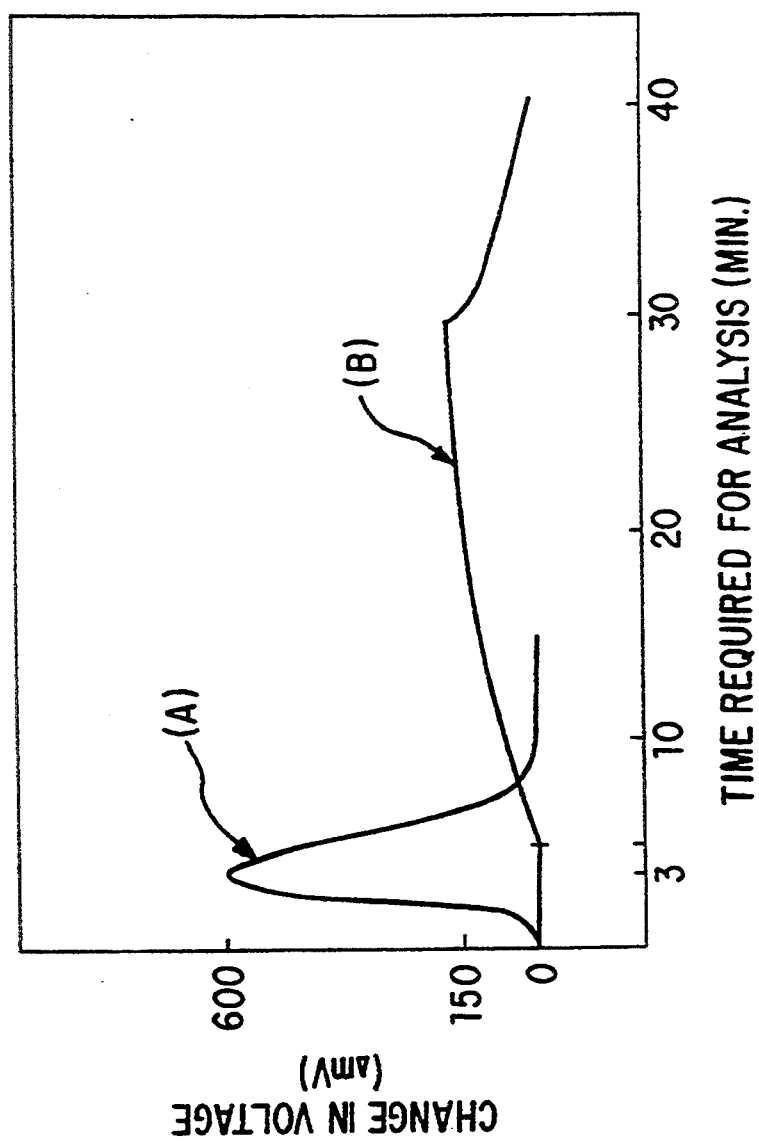
FIG. 9 shows a comparison of the sensitivity of the microbe membrane of the present invention and the sensitivity of a polyacrylamide/microbe membrane.

Two types of microbe sensor were made: One is the same type of microbe sensor made in Example 8 and the other is one that was made by mixing 0.4 mg (dry weight) of bacterial cells obtained in Example 1 with a 10 weight percentage acrylamide solution and subsequently gelating the mixture. These microbe sensors were inserted in the device described in Example 9 and were used to analyze BOD standard. FIG. 9 shows that, in 3-minute flow samples and a 66 ppm BOD standard concentration, the microbe sensor of the present invention produced 600 mV response (A) while the acrylamide/microbe sensor produced no response (B). In 30-minute flow samples and a 66 ppm BOD standard concentration, the acrylamide/microbe sensor produced 150 mV response. The microbe sensor of the present invention responds faster and is able to analyze BOD in a short period of time. Another disadvantage of the acrylamide/microbe sensor is that the sensor is susceptible to damage when inserted into the oxygen electrode with a slightly strong pressure.

EXAMPLE 13

Immobilization using Ultra-Filtration Membranes

Figure 10:
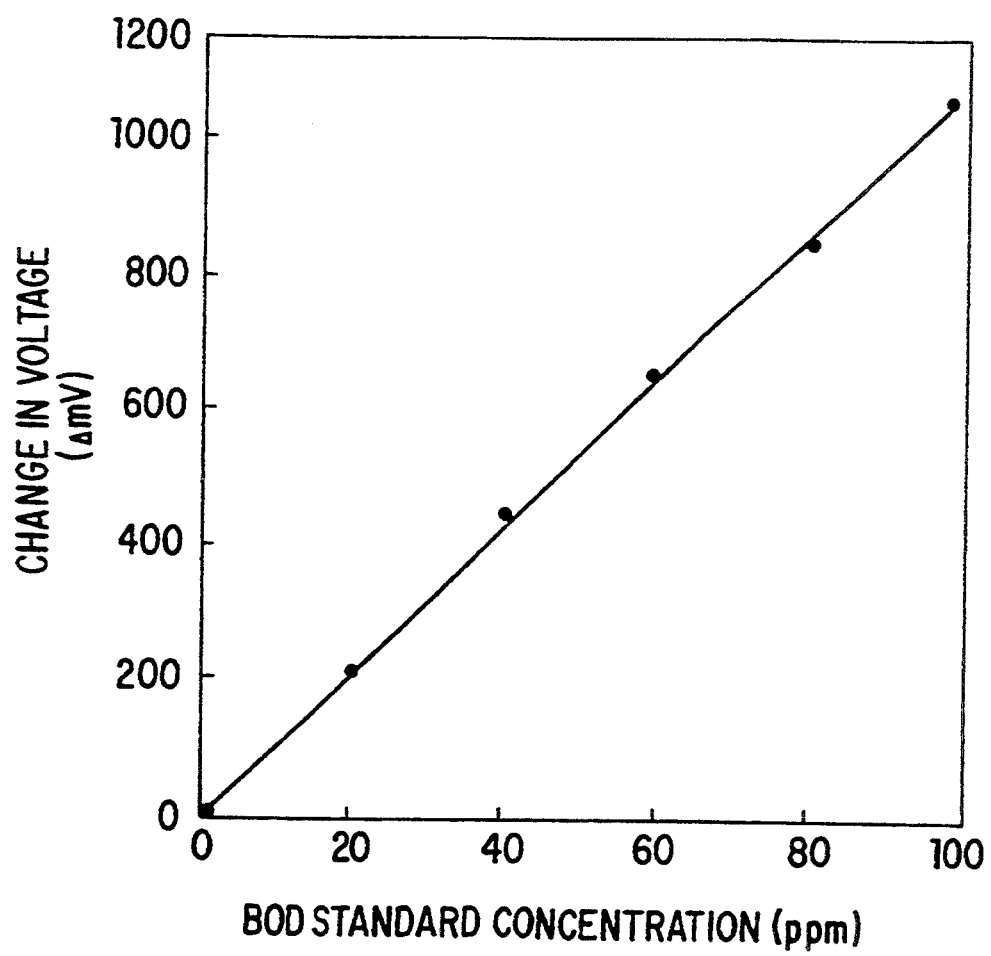
FIG. 10 is analysis of various concentrations of BOD standards using a BOD analyzer wherein the membrane is an asymmetric ultra-filtration membrane.

Bacterial cells obtained in Example 1 were immobilized on asymmetric ultra-filtration membranes (Filton ultra-filtration membrane, Omega-Membrane; Fuji Filter Co.,) by the method described in Example 8. The microbe sensor was inserted in the device described in Example 9 and was used to analyze BOD standard. As is shown in FIG. 10, a good relationship between a BOD standard concentration and the corresponding change in voltage of the oxygen electrode was obtained. The microbe sensor was also found to respond well.

EXAMPLE 14

Preparation of Microbe Membranes

Klebsiella oxytoca 12092 strain (FERM BP-3616) was inoculated into 100 ml of a liquid medium/pH6.5 (1% polypeptone, 0.1% yeast extract, 0.5% sodium chloride) in a 500-ml shaking culture flask and was incubated by shaking under aeration conditions at 30° C. for 17 hours.

After incubation, the culture was centrifuged at 600 rpm for 20 minutes. Bacterial cells thus obtained were suspended in a small amount of sterilized water. The suspension was centrifuged. The washing procedure was repeated three times. The bacterial cells were suspended to a final cell density, $OD_{660}$ of 0.58 (bacterial concentrate). 32 μl of the concentrate was suspended in 2 g of a mixture (1.7% K-carageenan, 0.8% locust bean gum). The mixture was dripped onto acetylcellulose membranes (Membrane filter type HA, an average pore size of 0.8 μm in diameter, Millipore Co.,). Suction was applied from the bottom side of the membrane until all the mixture was absorbed. The filtrate, a K-carageenan solution, was removed. The microbe membrane was cooled on ice and then immersed in 100 ml of a 40 mM phosphate buffer at room temperature for 5 minutes, K-carageenan and locust bean gum were solidified to give a microbe membrane.

EXAMPLE 15

Comparison of an Apparatus Having or Without Having an Outlet

BOD standard was analyzed using the microbe membrane obtained in Example 14. 220 ppm BOD standard prepared from a mixture (150 mg/L glucose and 150 mg/L glutamic acid) was diluted to a BOD concentration of 100 ppm and 5 ppm. The dilutions were used as samples.

Two apparatuses were used for comparison: One apparatus of FIG. 3 had an outlet 19, and the other did not have an outlet. A flow rate of air of the air pump was 1,000 ml/min., and a flow rate of washing solutions, BOD standard, and buffers was 4 ml/min., 4 ml/min., and 1 ml/min., respectively. These solutions were sent by a liquid-feeder pump.

A washing solution (water) was flushed for 10 minutes prior to BOD standard samples in order to stabilize a baseline. 100 ppm BOD standard was then flushed continuously. The initial point of a constant line of output was designated as an output value. A washing solution was flushed for 10 minutes, and then 5 ppm BOD standard sample was fed into a sampling inlet and flushed until an output value becomes constant.

Figure 11A:
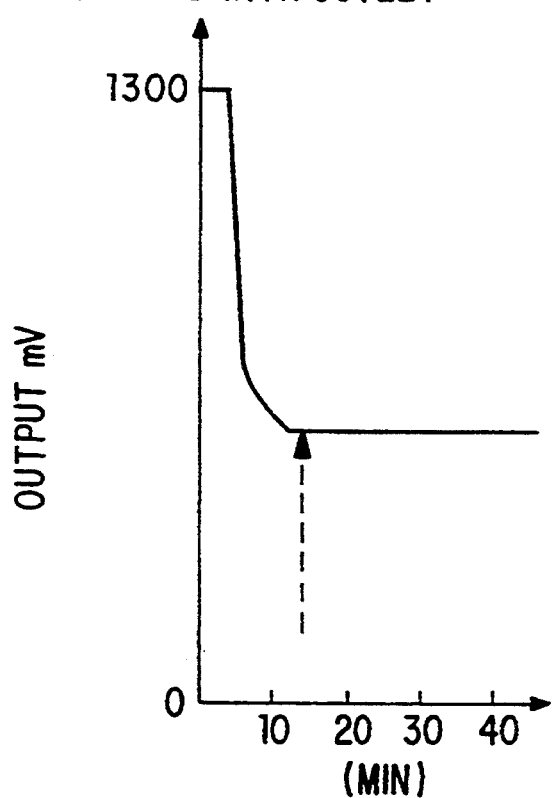
FIGS. 11A and 11B show a fluctuation of output of an oxygen electrode with or without an outlet.
Figure 11B:
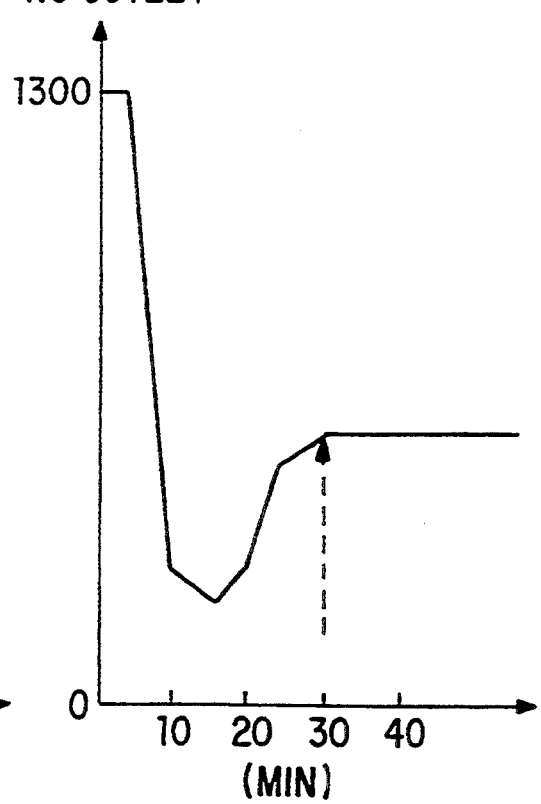

FIGS. 11A and 11B show the fluctuation of output of the oxygen electrode. The apparatus shown in FIG. 3 has a long passage between the BOD standard feeder and the flow cell. To prevent the passage from clogging with solid materials, the diameter of the passage was made larger so that it takes more time in analysis than the apparatus shown in FIG. 2, a simpler structure apparatus. The apparatus with an outlet have a peak output at 15 minutes while it takes 30 minutes for the apparatus without an outlet to stabilize output by an action of 100 ppm BOD standard.

EXAMPLE 16

Activation of Dry Microbe Membranes by Nutrition Solutions

Nutrition solutions contained 426 ppm glucose, 426 ppm glutamic acid, and 300 ppm yeast extract.

Microbe membranes were used the same ones prepared in Example 15. An apparatus was one having the outlet 19 described in Example 15. Other conditions were the same as those described in Example 15.

Figure 12:
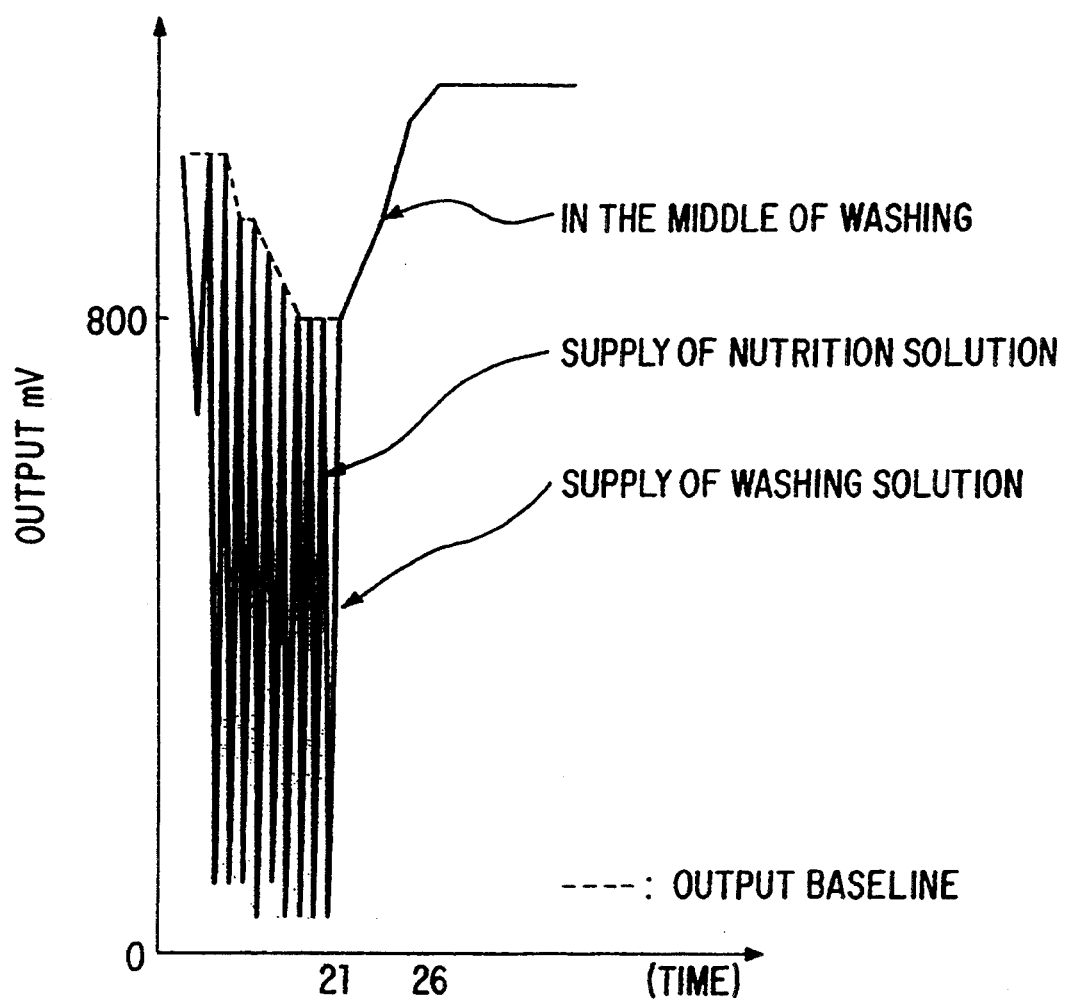
FIG. 12 shows activation of dried microbe membranes using nutrition solutions.

Nutrition solutions and buffers were supplied to 10 minutes each. The output is shown in FIG. 12. High output values indicate when dissolved oxygen concentration is high while low output values indicate when dissolved oxygen concentration is low.

As is shown in FIG. 12, once nutrition solutions are supplied to microbe membranes, substrates in nutrition solutions are consumed by microorganism in the membranes and dissolved oxygen concentration is reduced. Supply of nutrition solutions therefore reduces an output value. Subsequently, when washing solutions are supplied to microbe membranes, an output value is increased because no oxygen is consumed by the microorganism in the membrane due to the absence of substrates. Again, when nutrition solutions are supplied to the membrane, oxygen consumption is increased more than that resulted from the first supply of nutrition solutions because of the activation and growth of the microorganism by the first supply of nutritions, and an output value is further reduced. A cycle of supply of nutritions and washing water reduces an output value, which is measured when nutrition solutions are applied, due to further activation of microorganisms. At the same time, an output value is slow to increase when washing water is supplied, and an output baseline is gradually reduced. A reduced output baseline is believed to be the result from the increased activation of microorganisms. A constant output baseline suggests that the activation of microorganisms have reached a sufficient level for analysis.

The activation level of the microbe membrane increases by supply of nutrition solutions. However, microbe membranes having an elevated level of an output baseline are not suitable for analysis. To correct such microbe membranes, the microbe membranes have to be washed to stabilize an output baseline. Hence, supply of nutrition solutions should be stopped to the microbe membrane at the time when a certain level of activation was obtained, and washing solutions should be started flushing to stabilize an output baseline.

An output baseline that was considered the successful activation of microbe membranes was 1,000, 900, 800, and 700 mV, which was measured when nutrition solutions were supplied. When an output baseline has reached to the voltage, washing solutions were supplied to the microbe membranes. Analysis was carried out after a constant output was obtained. When an output has reached 800 mV or less, microbe membranes were washed, the procedure which produced the same output as that of microbe membranes before being dried (Table 8).

TABLE 8

| | |
|---|---|
| Activation of microbe membranes before drying | 100% |
| Activation of microbe membranes after drying | 50% |
| Activation of microbe membranes after drying (1,000 mV) | 55% |
| Activation of microbe membranes after drying (900 mV) | 73% |
| Activation of microbe membranes after drying (800 mV) | 90% |
| Activation of microbe membranes after drying (700 mV) | 90% |

The same activation level of microbe membranes was observed in an output baseline of 700 mV and 800 mV. It took approximately 26 hours to reach the activation level in an output baseline of 700 mV while it took approximately 21 hours to reach the activation level in an output baseline of 800 mV. Washing was started at approximately 21 hours after activation started, and was carried out until the baseline was stabilized. Five hours washing was found to be suitable for stabilization. It took totally 26 hours to complete activation and stabilization of microbe membranes. The activation level of the activated microbe membrane is shown in Table 9.

TABLE 9

| | |
|---|---|
| Activation of microbe membranes before drying | 100% |
| Activation of microbe membranes after drying | 50% |
| Activation of microbe membranes after drying | 90% |

As is evident from the above description, once dried microbe membranes activated by nutrition solutions are able to regain the sufficient activation level for analysis, they show the same level of output as that of original wet microbe membranes. Time required for activation is only 26 hours. In the methods of prior arts, it took two days for dried microbe membranes to be used for analysis: Dried microbe membranes are immersed in a buffer solution for one day, inserted in the device and alternately flushed with BOD standard and washing solutions. In the methods of prior art, BOD standard is used instead of nutrition solutions. The component of BOD standard is glucose and glutamic acid but no vitamins and metal salts. It takes one more day to activate dried microbe membranes so as to regain sufficient activation for analysis. Therefore, the activation method of the present invention shortens 22 hours for the activation of dried microbe membranes.

EXAMPLE 17

Effect of Intermittent and Continuous Supply of Solutions on the Retention of the Activation Level of Microbe Membranes In the following, microbe membranes prepared as in Example 14 were used. A flow rate of solutions was 5 ml/min., and the operation time was 16 hours. The same apparatus described in Example 16 was used.

Condition 1: Intermittent supply of washing solutions and BOD standard

Time of pumping; 30 seconds
No pumping; 90 seconds

Figure 13:
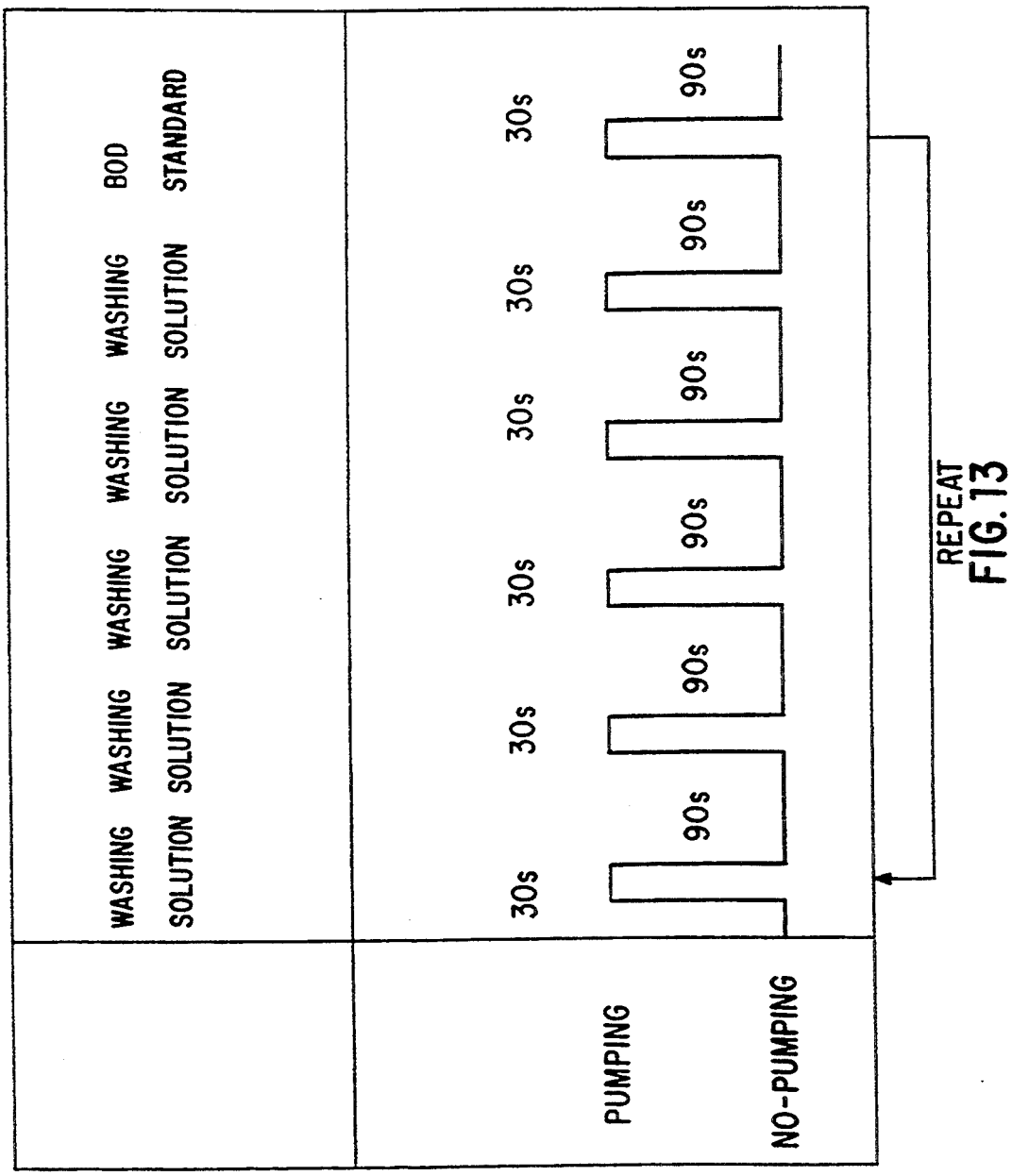
FIG. 13 shows a timetable of intermittent supply of solutions.
Figure 14:
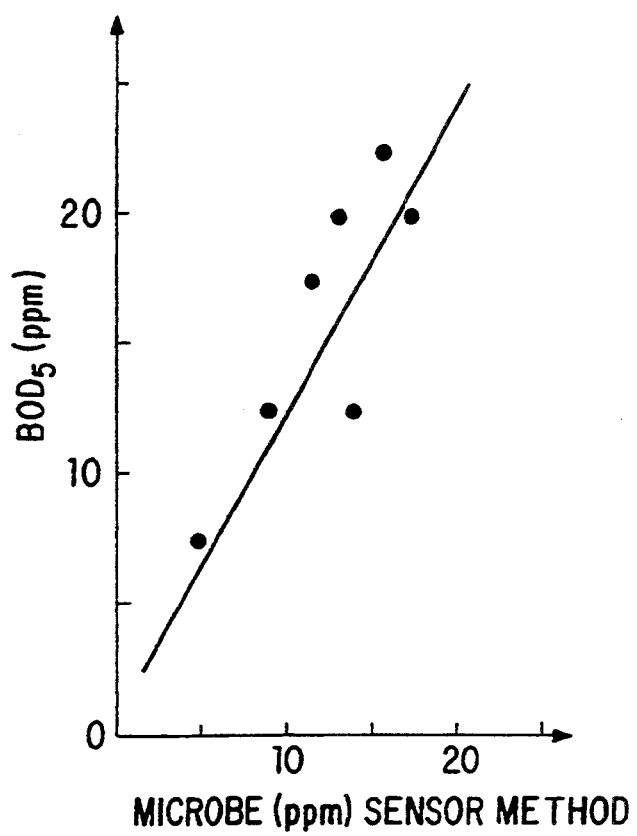
FIG. 14 is a correlation between the microbe sensor method of the invention and the 5-day method.

As is shown in FIG. 13, washing solutions were flushed from the first pumping to the fifth pumping and BOD standard was flushed at the sixth pumping. This cycle was repeated.

Condition 2: Continuous supply of washing solution s and BOD standard

Washing solutions; 11 minutes
50 ppm BOD standard; 4 minutes
This cycle was repeated.

The results are shown in Table 10. In the intermittent pumping, consumed washing solutions, BOD standard, and buffer solutions were about 1.2 liters, which was ¼ of continuous pumping. However, the activation level of microbe membranes in the intermittent pumping is equivalent to that of the continuous pumping.

TABLE 10

| Activation of microbe membranes before activating by condition I | Activation of microbe membranes after 16 hrs. | |
|---|---|---|
| | Activation of microbe membranes after activating | Activation of microbe membranes after activating by condition 2 |
| 100% | 93% | 93% |

EXAMPLE 18

Effect of Preservatives on the Activation of Microbe Membranes (1) Activation (output) of microbe membranes was compared: one is that various preservatives were added to washing solutions, buffer solutions, and BOD standard, and the other is that no preservative was added to these solutions.

The first activation (output) analysis was compared to the average of 10 activation analyses, using 50 ppm BOD standard. The results are shown in Table 11.

TABLE 11

| Preservatives | Activation level of microbe membranes* |
|---|---|
| Phenol (0.1%) | 68% |
| Sodium salicylate (0.75%) | 77% |
| Sodium hypochlorite (0.01%) | 74% |
| Boric acid (0.5%) | 93% |

TABLE 11-continued

| Preservatives | Activation level of microbe membranes* |
|---|---|
| Potassium sorbic acid (0.5%) | 93% |

*Initial activation level of microbe membranes is taken as 100%.

As is shown in Table 11, boric acid and potassium sorbic acid are the best preservatives for the activation of microbe membranes.

(2) The presence and absence of microorganism clusters on the surface of microbe membranes were visually observed. Boric-acid-added washing solutions, buffers, and BOD standard were added to the microbe membrane of the present invention. Wastewater from a food plant was analyzed using the membrane. When wastewater was not analyzed, the microbe membrane was exposed to the condition 2 in Example 17 to maintain its activated level. Microorganism clusters were then measured. The results are shown in Table 12.

TABLE 12

| Concentration of added boric acid | Bacterial cluster | |
|---|---|---|
| | At 0 day | At 10 day |
| 0% | None | Present |
| 0.3% | None | None |
| 0.5% | None | None |
| 1.0% | None | None |

*When 1.0% boric acid was added, microbe membranes were affected. Although the microbe membranes were able to be used for analysis, it took more than 24 hours to activate the membranes.

As is shown in Table 12, a preferable boric acid concentration is 0.3–0.5%.

(3) The number of colonies was counted on the microbe membrane by placing the membrane in 50 ppm BOD standard (pH2.0, adjusted with hydrochloric acid) under the condition shown in Table 12, at 30° C. for 10 days. The results are shown in Table 13.

TABLE 3

| Preservative | Number of colony | |
|---|---|---|
| | At 0 day | At 10 day |
| Not added | 0/ml | $10^7$/ml |
| 0.3% Boric acid | 0/ml | $10^3$/ml |
| 0.3% Boric acid/pH 2.0 adjusted with hydrochloric acid | 0/ml | 10 or less/ml |

EXAMPLE 19

Correlation Between the 5-Day Method (JIS method) and the Method of the Present Invention (Microbe Sensor Method)

Conditions: Microbe membranes were prepared as is described in Example 14.

The microbe membrane was activated as described in Example 16. Boric acid was added to washing solutions, buffers, BOD standard to a final concentration of 0.3%. The pH of these solutions was adjusted with hydrochloric acid to 2.0.

The activation level of the microbe membrane was maintained as described in Condition 1 of Example 17.

Methods: Samples were taken from wastewater from a food plant once a day and analyzed by the 5-day method and the microbe sensor method. The correlation between these methods was analyzed. The correlation coefficient is as high as 0.95 or more, suggesting a

EXAMPLE 20

Continuous Use of the Microbe Sensor

To investigate the correlation between the 5-day method and the microbe sensor method as well as retention time of the activation level of the microbe membrane, the microbe membrane of the present invention was used for continuous BOD analysis under the same condition as in Example 19.

Figure 15:
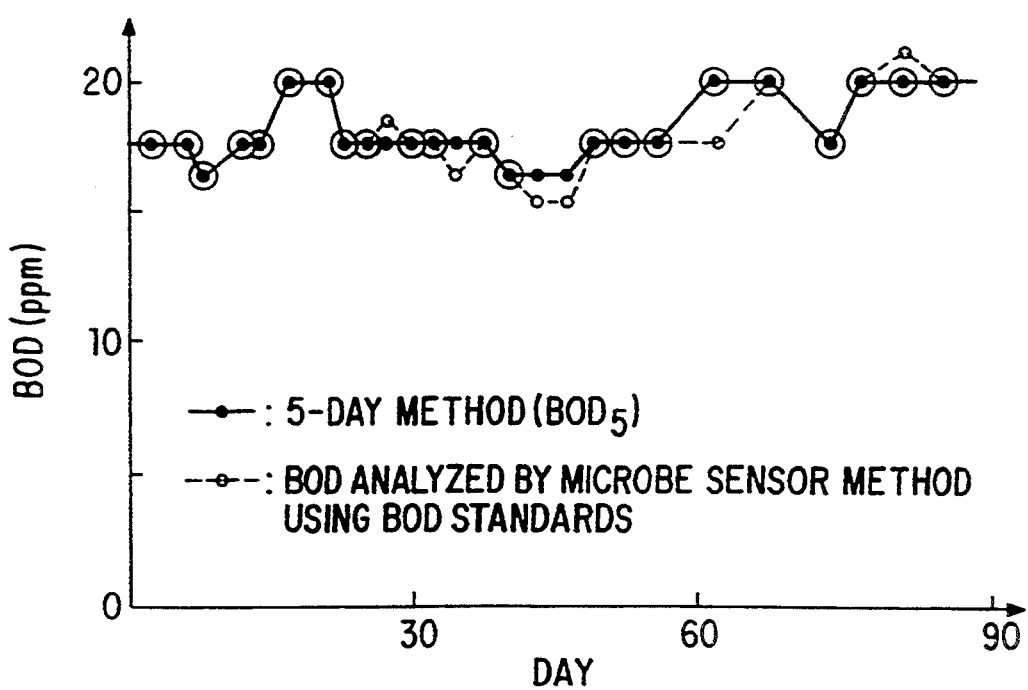
FIG. 15 is continuous BOD analysis by the microbe sensor method of the invention and the 5-day method.

There is a high correlation between these two methods even in continuous use. In addition, the microbe membrane can be used for 3 months (see FIG. 15).

As is evident from the above description, it takes 5 days for the JIS method to analyze BOD. In contrast, the present invention provides a quick BOD analysis and an easy monitoring system for the routine testing of wastewater.

What is claimed is:

1. A biologically pure culture of *Klebsiella oxytoca* FERM BP-3616 that is resistant to arsenic.

2. A porous membrane containing the microorganism *Klebsiella oxytoca* FERM BP-3616, immobilized in pores of the membrane by means of a gelating agent.

3. The membrane according to claim 2, wherein said membrane is formed of a hydrophilic material.

4. The membrane according to claim 3, wherein the pores have an average pore size of about 0.65–3 $\mu$m.

5. The membrane according to claim 3, wherein the gelating agent is selected from at least one of the group consisting of alginic acid and salts thereof, agar, gellan gum, xanthane gum, gelatine, carrageenan, locust bean gum, methylcellulose, pectin, and pullulan.

* * * * *

UNITED STATES PATENT AND TRADEMARK OFFICE
CERTIFICATE OF CORRECTION

PATENT NO. : 5,426,042
DATED : June 20, 1995
INVENTOR(S) : Maeda, et. al.

It is certified that error appears in the above-indentified patent and that said Letters Patent is hereby corrected as shown below:

Title page, item "[*] Notice" should read--The term of this patent shall not extend beyond the expiration date of Pat. No. 5,356,792--.

Signed and Sealed this

Twenty-first Day of November, 1995

*Attest:*

BRUCE LEHMAN

*Attesting Officer*  *Commissioner of Patents and Trademarks*